United States Patent [19]

Aswell et al.

[11] Patent Number: 4,588,561

[45] Date of Patent: May 13, 1986

[54] PACKAGE FOR REMOVING OXYGEN FROM A GASEOUS MIXTURE

[75] Inventors: James E. Aswell, New Freedom, Pa.; William E. Moritz, III, Reisterstown, Md.

[73] Assignee: Becton, Dickinson and Company, Paramus, N.J.

[21] Appl. No.: 628,670

[22] Filed: Jul. 6, 1984

[51] Int. Cl.⁴ ............................................... B01J 7/02
[52] U.S. Cl. .................................... 422/238; 422/239; 252/188.28; 435/801; 435/810
[58] Field of Search .................. 422/61, 86, 222, 236, 422/238, 239, 305; 435/287, 801, 810; 252/188.28; 502/173

[56] References Cited

U.S. PATENT DOCUMENTS

| | | | |
|---|---|---|---|
| 2,825,651 | 3/1958 | Loo et al. | 252/188.28 |
| 2,908,555 | 10/1959 | Grosskopf | 422/86 |
| 3,246,959 | 4/1966 | Brewer | 435/801 |
| 4,038,148 | 7/1977 | Miller et al. | 422/61 |
| 4,200,610 | 4/1980 | Swaine et al. | 435/801 |
| 4,230,595 | 10/1980 | Yamaji et al. | 252/188.28 |
| 4,287,306 | 9/1981 | Brewer | 422/86 |
| 4,299,719 | 11/1981 | Aoki et al. | 252/188.28 |
| 4,377,554 | 3/1983 | Johnson | 422/236 |

FOREIGN PATENT DOCUMENTS 8200599  3/1982  Int'l Pat. Institute ......... 252/188.28

Primary Examiner—David L. Lacey
Attorney, Agent, or Firm—James R. McBride

[57] ABSTRACT

A package is provided for removal of all or part of the oxygen in a gaseous atmosphere within the package. The package includes a gas impermeable, sealable container having a sachet disposed therein. The sachet contains an oxygen reactive material, preferably powdered iron. A compartment is provided within the container which is in fluid communication with the sachet location. The compartment is adapted to receive a predetermined level of water.

13 Claims, 4 Drawing Figures

PACKAGE FOR REMOVING OXYGEN FROM A GASEOUS MIXTURE

FIELD OF THE INVENTION

The present invention relates generally to an apparatus and method for the generation of an anaerobic or microaerophilic atmosphere which is conducive to the growth of certain microorganisms.

DESCRIPTION OF THE PRIOR ART

It is well known that some microorganisms require an aerobic atmosphere for growth, others require an anaerobic atmosphere, and still others require a microaerophilic atmosphere in which the oxygen level is between aerobic and anaerobic. In addition, some microorganisms require elevated levels of carbon dioxide for enhanced growth.

The attainment of an aerobic atmosphere is relatively simple, in most cases merely requiring aeration of the culture media. Anaerobic conditions are more difficult to attain and the prior art contains many devices and processes for producing anaerobic atmospheres. U.S. Pat. No. 3,246,959, to Brewer discloses a device for generating such anaerobic atmospheres by generation of hydrogen for reaction with oxygen in the atmosphere of a gas-tight apparatus such as that disclosed in U.S. Pat. No. 3,483,089 to Brewer. The reaction between the hydrogen and oxygen is catalyzed by a platinum catalyst in the anaerobic apparatus.

U.S. Pat. No. 4,347,222 to Beall discloses disposition of the catalyst in one receptacle of a unitary apparatus. This apparatus requires means for puncturing seals between several of the receptacles. The puncture means is supplied by a device which is separate from the gas generating apparatus or as part of a mated container.

The reaction between hydrogen and oxygen in the presence of a catalyst is strongly exothermic. Flashing, and even explosion, can occur at the catalyst surface, particularly if the catalyst is finely divided and no means are provided to dissipate the heat generated.

U.S. Pat. No. 4,013,422 to Spinner discloses a container having a material for generating a reducing gas, such as hydrogen, for reaction, in the presence of a catalyst, with oxygen. The Spinner apparatus, however, uses an exposed catalyst pellet with no provision for heat removal. In addition, it relies on the breaking of an ampoule containing a liquid and thereby instantaneous release of the liquid into contact with the material for generating the reducing gas. Thus no means are provided for controlling the rate at which the contact is made. Experience has shown that contact at a slow and controlled rate is essential for accurate attainment of pre-determined final oxygen levels, particularly in those cases where it is desired to reduce, but not eliminate, the oxygen in the atmosphere.

U.S. Pat. No. 4,287,306 to Brewer describes a further apparatus for generating anaerobic atmospheres. In accordance with this patent, a flexible sealed package is provided with a catalyst coated onto the exterior surface of the package for use in catalyzing the reaction between oxygen outside the package and hydrogen generated within the package. This apparatus, like the Spinner apparatus, has the disadvantage of exposed active catalyst.

U.S. Pat. No. 4,289,855 to Whitley discloses a safety catalyst package designed to reduce the danger of flashing or explosion. The Whitley package encloses a catalyst within holes and folds in a metal foil net. The net, which is inside of a container having holes for gas exchange, is composed of a heat conducting material, and thereby functions to remove heat from the catalyst vicinity. The Whitley disclosure is of a safety catalyst package only, and makes no provision for supply of hydrogen.

A package, for use in an anaerobic jar and specifically designed for attainment of a microaerophilic atmosphere, is disclosed in U.S. Pat. No. 4,377,554 to Johnson. The Johnson invention relies on control of "wetover" and "condensation" times for successful generation of microaerophilic atmospheres, and uses conventional exposed catalysts attached either to the outside of the package or to the lid of the jar.

A cardboard package for use in generating an anaerobic atmosphere is commercially available from the BBL Microbiology Systems Division of Becton Dickinson Company. This package includes a catalyst chamber mounted in the side of the box. The catalyst chamber is porous on both sides to permit generated hydrogen to flow through the chamber and thus react with the catalyst.

The prior art discussed above generally describes apparatus for attaining an anaerobic atmosphere wherein hydrogen is generated and caused to react with the oxygen present in a vessel by means of a catalyst. Great Britain Pat. No. 2109406 to Kasugai describes a process for culturing anaerobic bacteria wherein an agent which is reactive with oxygen is enclosed in an air tight closed vessel. The agent contains a composition which is capable of removing oxygen and generating carbon dioxide in a volumetric ratio of about approximately twice as much oxygen removed as carbon dioxide generated. The preferred oxygen reactive material disclosed in the Kasugai patent is powdered iron.

SUMMARY OF THE INVENTION

In accordance with one embodiment of the present invention, there is provided a package for removing all or part of the oxygen in a gaseous atmosphere within the package. The package includes a gas impermeable, sealable container having a sachet disposed therein. The sachet contains an oxygen reactive material. A compartment is provided within the container which is in fluid communication with the sachet location. The compartment is adapted to receive a predetermined level of water.

In use, one or more petri dishes having a prepared media and having been inoculated with a sample suspected of containing an anaerobic microorganism are inserted into the container adjacent to the sachet. A pipette or a vial is then used to dispense a predetermined level of water into the compartment. The water hastens reaction between any oxygen contained within the envelope and the oxygen reactive material. The container is then sealed by suitable means. In a preferred embodiment of the invention the container is a flexible envelope and oxygen reactive material is powdered iron. The oxygen reacts with the powdered iron to form iron oxide. After a suitable period of time has elapsed the oxygen level contained within the envelope is reduced to a level appropriate for the growth for anaerobic organisms, e.g. less than about 2 percent by volume.

The present invention provides an extremely simple, easily used, self contained device for generation of an anaerobic atmosphere without the hazards associated with the use of hydrogen and a catalyst.

BRIEF DESCRIPTION OF THE DRAWINGS

FIG. 4 is a view of the water containing vial of the invention showing the arrangement of the tear strip used to seal the end of the vial.

DETAILED DESCRIPTION OF THE INVENTION

Figure 1:
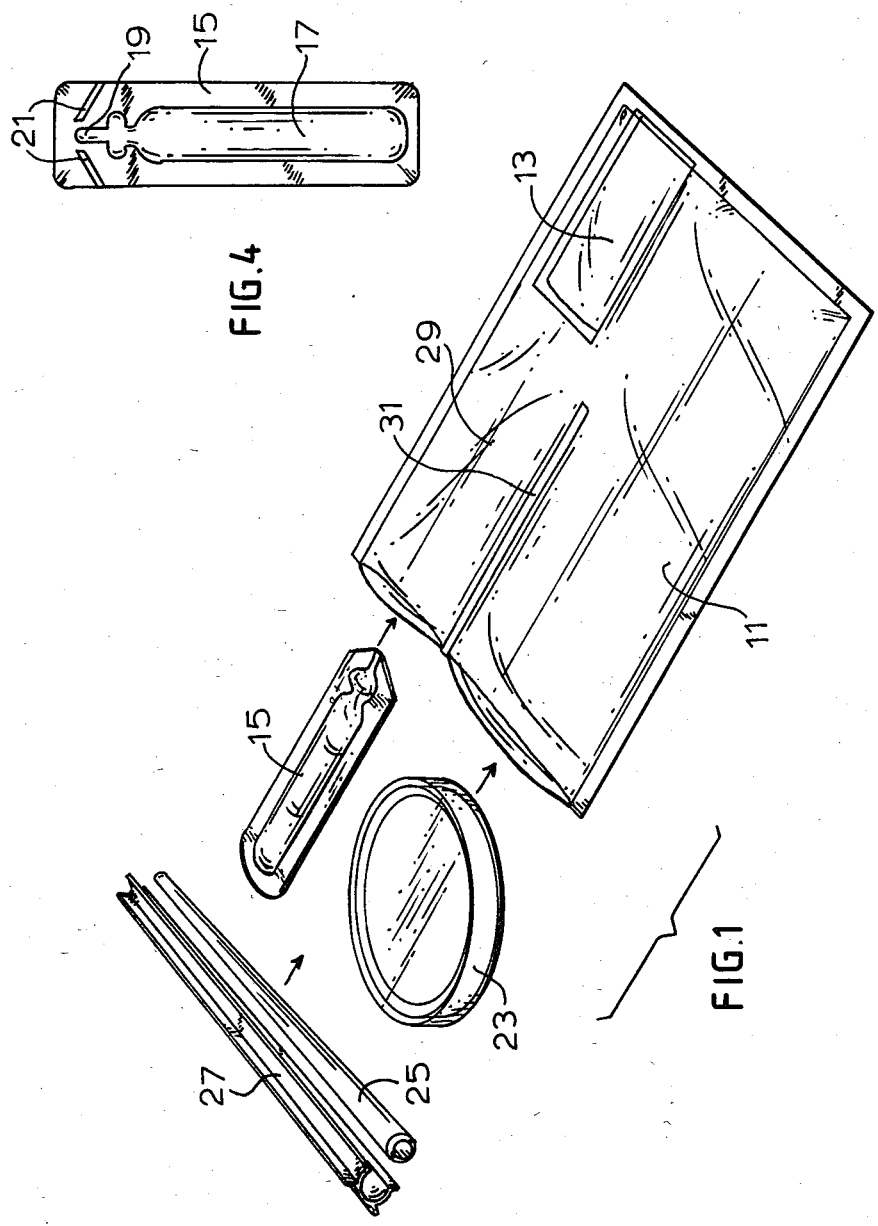
FIG. 1 is an exploded view of the anaerobic generating apparatus of the invention showing the sequence of assembling the package.

Referring now to FIG. 1, there is shown a package for removing oxygen from a gaseous atmosphere. The package is in the form of an envelope 11. Envelope 11 is made of a suitable material which is impervious to the atmosphere and moisture. Thus, for example, the envelope 11 may be formed of a laminated plastic material, such as polyvinyldichloride/polyester/polyethylene. The envelope 11 may be formed from two panels suitably secured together around the edges by heat sealing.

The interior of the envelope contains a sachet 13 which includes an oxygen reactive material. The sachet 13 is secured in place within the envelope 11 by any suitable means. One suitable means is to place one edge of the sachet between the two panels of plastic which are used to form the envelope prior to heat sealing and to heat seal the plastic over a portion of the sachet. Another suitable means would be to heat seal an area of the envelope adjacent to the sachet so as to provide an open pocket for restraining the sachet in a suitable position. The sachet is formed of a porous material, such as water resistant paper, to permit the water to penetrate to the inside of the sachet and to permit reaction of the gaseous atmosphere within the envelope with the contents of the sachet.

As indicated, the sachet contains a material which is reactive with oxygen so as to remove the oxygen from the gaseous atmosphere within the envelope. A suitable oxygen reactive material is a metal powder provided in a reduced state of oxgenation. Suitable metal powders include iron, copper, aluminum. A preferred metal powder is powdered iron. It has been determined that the use of iron powder having a particle size 95 percent less than 325 mesh U.S. Standard Sieve Size is a most preferred oxygen reactive material for use in the invention.

For an embodiment of the invention wherein it is desired to provide an atmosphere having a predetermined level of carbon dioxide, a carbon dioxide generating composition is provided. The carbon dioxide generating composition includes a water soluble solid acid and a water soluble carbonate in amounts suitable for generating carbon dioxide. As representative examples of suitable acids there may be mentioned: citric, tartaric, ascorbic, succinic, malic, fumaric, lactic acids and the like. As representative examples of suitable carbonates, there may be mentioned: sodium bicarbonate, sodium carbonate, potassium carbonate, sodium sesquicarbonate, etc. A preferred composition includes citric acid and sodium bicarbonate. The carbon dioxide generating composition is preferably employed in the form of a powder which is 100 percent less than 200 mesh U.S. Standard sieve size and which is dispersed with the powdered iron.

It has also been determined that to provide a suitable low level of oxygen required for anaerobic conditions within an appropriate time, the presence of a water absorbing filler is important. Suitable fillers include diatomaceous earth, charcoal, cellulose fiber, silica gel and barium sulfate. In particular, diatomaceous earth has been found to be suitable to provide water absorptive properties and iron powder spacing properties. The filler is preferably 100 percent less than 200 mesh U.S. Standard Sieve Size. A surfactant is also advantageous to provide water dispersive properties and wetting properties to the oxygen reactive composition of the invention. Suitable surfactants include sodium laurel sulfate, polysorbate and sodium dodecyl sulfate.

Preferably, the powdered iron is present in the composition at a level of from about 25 to about 35 percent, the filler is present at a level of from about 40 to about 60 percent, the acid is present at a level of from about 12 to about 21 percent, the carbonate is present at a level of from about 1 to about 4 percent and the surfactant is present at a level of from about 0.05 to about 0.4 percent. In a most preferred composition, the powdered iron is present at a level of from about 28 to about 30 percent, the diatomaceous earth is present at a level of from about 50 to about 54 percent, the acid is present at a level of from about 15.5 to about 17.5 percent, the carbonate is present at a level of from about 1.7 to about 2.7 percent and the surfactant is present at a level of from about 0.15 to about 0.25 percent. All percentages used herein are by weight, unless otherwise indicated.

In general, the oxygen reactive composition of the present invention should be present in the container at a level of from about 4.5 to 6.0 grams, preferably from about 4.7 to about 5.6 grams, for providing suitable oxygen reactive properties with a volume of air of from about 250 cc to 350 cc. This size of container is sufficient to process one or two petri dishes. Preferably, the container is a flexible, plastic, gas impermeable envelope having a width of from about 14 to about 18 cm and a length of from about 23 to about 30 cm. Of course, the envelope can have any length longer than the preferred length since the excess length can be compensated for during the process of sealing the bag. The envelope has a compartment 29 formed therein by heat sealing a section 31 as shown in FIG. 1.

The goal of the present invention is to attain less than 2 percent oxygen within the container and from about 4 to about 12 percent carbon dioxide within the container in a period of less than about 2 hours. To achieve this goal, it has been determined that the level of water added to the oxygen reactive composition of the invention is critical. To achieve the oxygen reducing goal of the invention, the water should be added to the composition at a level of from about 60 to about 80 percent of the weight of the oxygen reactive composition. Most preferably, the water should be added to the composition at a level of from about 65 to abot 75 percent of the weight of the composition. In one embodiment of the invention, the oxygen reactive material in the sachet can be premoistened with a suitable level of water prior to sealing of the package without insertion of the petri dish or dishes. The oxygen within the package is removed by reaction with the oxygen reactive material, which retains a residual ability to react with additional oxygen. The package can then subsequently be reopened for insertion of the petri dish and reaction with the oxygen introduced by the reopening of the package.

In a preferred embodiment of the invention, a suitable predetermined level of water is provided for use with the oxygen reactive composition of the invention as a separate vial, 15, as shown in FIG. 4. The water containing vial 15 is made of heat sealed plastic having a tube 17 shaped therein. A spout 19 is provided at the end of the tube. The spout can be opened by use of the tear strip 21 provided in the vial.

In use, as shown in FIG. 1, the end of the vial is torn from the vial to expose the tip of the spout and the vial is inserted within the envelope 11 into compartment 29 in fluid communication with the sachet containing the oxygen reactive material. One petri dish miniteter panels or microtiter-type panels 23 are inserted in the container and the container is sealed.

Figure 2:
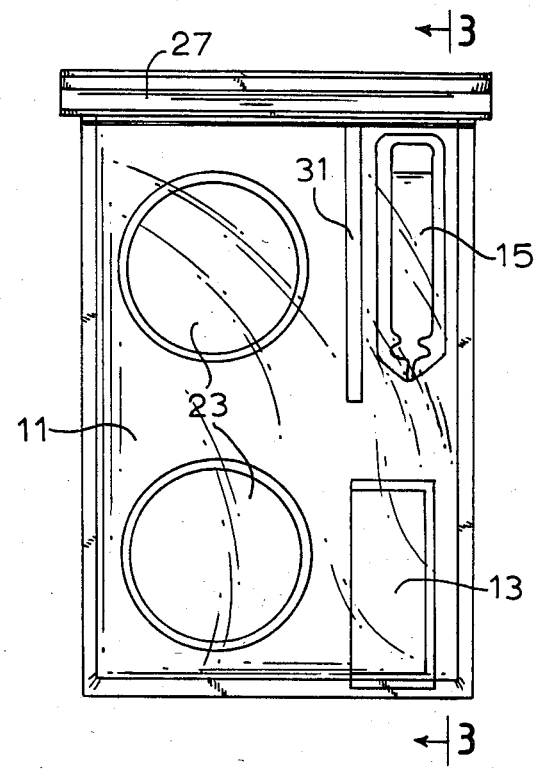
FIG. 2 is a front view of the assembled package.
Figure 3:
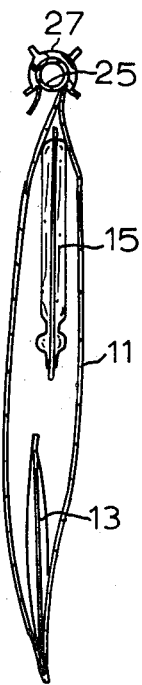
FIG. 3 is a side view of the assembled package.

A suitable means for sealing a flexible envelope is shown in FIGS. 1 and 2. As shown in FIG. 2, the open end of the envelope 11 is wrapped around tubular rod 25. A semi-circular clamping rod 27 is clamped over the end of the envelope and the rod 25, as shown in FIG. 2. The water is then dispensed from the vial by squeezing the vial while it is in place in the envelope. Thereafter, the package is placed in a suitable incubation temperature for generation of an oxygen free atmosphere and growth of the anaerobic organism.

In a commerical embodiment of the present invention, a plurality of envelopes having the sachet suitably positioned in the envelope would be packaged with a matching plurality of vials containing a predetermined level of water. The package would include at least one device for sealing the end of the envelope.

The following examples further illustrate various features of the present invention but are intended to in no way limit the scope of the invention which is defined in the appended claims.

EXAMPLE

An oxygen reactive and carbon dioxide generating composition is prepared by blending together the following materials:

| Oxygen Reactive Material | |
|---|---|
| Material | % by Weight |
| Keselguhr (diatomaceous earth from J. T. Baker, Catalog No. 2244) | 51.6 |
| Powdered Iron (95% less than 325 mesh U.S.S. obtained from Glidden Co. (A-131 SCM) | 29.2 |
| Citric Acid (anhydrous, free flowing powder) | 16.7 |
| Sodium Carbonate (amorphous powder) | 2.3 |
| Sodium Lauryl Sulfate (crystals) | 0.2 |

The above blend of materials was placed in a ball mill and milled for one hour to uniformly disperse the materials.

Sachets were prepared having 5.14+0.4 grams of the above oxygen Reactive Material. The sachets were prepared using the same porous water-resistant paper as are used for the preparation of tea bags.

The sachets were placed in position between two 16 cm×27 cm sheets of heat sealable gas impermeable plastic, comprising a lamination of polyester, polyvinyldichloride and polyethylene, with the polyester layer being the inside layer. The sachet was located near a corner of the sheets. The sheets were then heat sealed around three sides to form an envelope. The sachet was located in a position such that the bottom heat seal line passed over an edge of the sachet to secure the sachet in place. An additional heat seal line was provided to form a compartment extending from the top of the envelope and above the sachet.

3.5 grams of water were pipetted into the compartment above the sachet and the envelope was sealed. The oxygen level in the envelope after a period of two hours was found to be 1.18 percent by volume.

What is claimed is:

1. A package for removing oxygen from a gaseous mixture within a confined space comprising:
   (1) a sealable envelope
   (2) a gas permeable sachet located within said envelope containing (1) an oxygen reactive material selected from the group consisting of iron powder, copper powder and aluminum powder, (2) a carbon dioxide generating composition including a water soluble, solid acid and a water soluble carbonate, (3) a filler selected from the group consisting of diatomaceous earth, charcoal, cellulose fiber, silica gel and barium sulfate and (4) a water dispersive and wetting surfactant,
   (c) a compartment within said envelope in fluid communication with said sachet location for receiving a predetermined level of water.

2. A package in accordance with claim 1 wherein said oxygen reactive material is iron powder having a particle size 95% less than 325 mesh U.S. Standard Sieve Size.

3. A package in accordance with claim (1) wherein said water soluble carbonate is selected from the group consisting of sodium bicarbonate, sodium carbonate, potassium carbonate, sodium sesquicarbonate and said water soluble acid is selected from the group consisting of citric acid, tartaric acid, ascorbic acid, succinic acid, malic acid, fumaric acid and lactic acid.

4. A package in accordance with claim (1) wherein said filler is diatomaceous earth having a particle size of 100% less than 200 mesh U.S. Standard Sieve Size.

5. A package in accordance with claim 1 wherein said sachet is fixed to said envelope.

6. A package in accordance with claim 1 which further comprises a separate vial containing a predetermined level of water.

7. A package in accordance with claim 1 wherein said oxygen reactive material comprises said powdered iron at a level of from about 25 to about 35%, said filler at a level of from about 40 to about 60%, said water soluble acid at a level of from about 12 to about 20%, said water soluble carbonate at a level of from about 1 to about 4% and said surfactant at a level of from about 0.05 to about 0.4%.

8. A package in accordance with claim 7 wherein said package further includes a vial containing water at a level of from about 60 to about 80% by weight of water based on the weight of said oxygen reactive material.

9. An article for use in removing oxygen from a gaseous mixture in a confined space comprising:
   a gas permeable sachet having the following components disposed therein:
   (1) an oxygen reactive material selected from the group consisting of iron powder, copper powder and aluminum powder,
   (2) a carbon dioxide generating composition including a water soluble, solid acid and a water soluble carbonate, (3) a filler selected from the group consisting of diatomaceous earth, charcoal, cellulose fiber, silica gel and barium sulfate; and (4) a water dispersive and wetting surfactant.

10. An article in accordance with claim 9 wherein said oxygen reactive material is iron powder having a particle size 95% less than 325 mesh U.S. Standard Sieve Size.

11. An article in accordance with claim 9 wherein said water soluble carbonate is selected from the group consisting of sodium bicarbonate, sodium carbonate, potassium carbonate, sodium sesquicarbonate and said water soluble acid is selected from the group consisting of citric acid, tartaric acid, ascorbic acid, succinic acid, malic acid, fumaric acid and lactic acid.

12. An article in accordance with claim 9 wherein said filler is diatomaceous earth having a particle size of 100% less than 200 mesh U.S. Standard Sieve Size.

13. An article in accordance with claim 9 wherein said oxygen reactive material comprises said powdered iron at a level of from about 25 to about 35%, a filler at said level of from about 40 to about 60%, said water soluble acid at a level of from about 12 to about 20%, said water soluble carbonate at a level of from about 1 to about 4% and said surfactant at a level of from about 0.05 to about 0.4%

* * * * *